(12) United States Patent
Mansour et al.

(10) Patent No.: US 12,171,976 B2
(45) Date of Patent: Dec. 24, 2024

(54) FLUID FLOW CONTROL BY A NON-PINCHING VALVE

(71) Applicant: CareFusion 303, Inc., San Diego, CA (US)

(72) Inventors: George Mansour, Diamond Bar, CA (US); Chris Zollinger, Chino Hills, CA (US); Jonathan Yeh, Diamond Bar, CA (US); Christopher J. Clarke, Walton on Thames (GB)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/128,639

(22) Filed: Mar. 30, 2023

(65) Prior Publication Data

US 2023/0233831 A1     Jul. 27, 2023

Related U.S. Application Data

(60) Continuation of application No. 16/428,264, filed on May 31, 2019, now Pat. No. 11,642,510, which is a
(Continued)

(51) Int. Cl.
*A61M 39/22* (2006.01)
*A61M 5/142* (2006.01)
*A61M 5/168* (2006.01)

(52) U.S. Cl.
CPC ............ *A61M 39/22* (2013.01); *A61M 5/142* (2013.01); *A61M 5/16813* (2013.01);
(Continued)

(58) Field of Classification Search
CPC ...... A61M 2039/224; A61M 2039/226; A61M 2039/229; A61M 39/22; A61M 39/223;
(Continued)

(56) References Cited

U.S. PATENT DOCUMENTS 3,111,299 A * 11/1963 Miller ................... F16K 27/065
251/316
4,064,909 A    12/1977 Neward
(Continued)

FOREIGN PATENT DOCUMENTS

DE     202011108910     3/2012
EP        1557187       7/2005
(Continued)

OTHER PUBLICATIONS

Australian Examination Report No. 1 for Application No. 2017200833, dated Sep. 19, 2018, 7 pages.
(Continued)

*Primary Examiner* — Shefali D Patel
(74) *Attorney, Agent, or Firm* — Morgan, Lewis & Bockius LLP

(57) ABSTRACT

A pumping system comprising a pump comprising a door for access within a housing of the pump, a pump segment configured for conveying a fluid based on compression of the pump segment, a pump segment frame for preventing said pump segment from stretching, a visual placement indicator configured for facilitating in a proper placement of the pump segment frame in the housing, and a non-pinching valve configured to be disposed in the housing and to control a flow of the fluid without requiring pinching of a tube.

17 Claims, 15 Drawing Sheets

Related U.S. Application Data division of application No. 13/525,205, filed on Jun. 15, 2012, now Pat. No. 10,350,402.

(52) U.S. Cl.
CPC .... *A61M 5/16877* (2013.01); *A61M 5/16881* (2013.01); *A61M 39/223* (2013.01); *A61M 2039/224* (2013.01); *A61M 2039/226* (2013.01); *A61M 2039/229* (2013.01); *Y10T 137/85986* (2015.04)

(58) Field of Classification Search
CPC .. A61M 5/142; A61M 5/168; A61M 5/16804; A61M 5/16813; A61M 5/16877; A61M 5/16881; Y10T 37/85978; Y10T 37/85986; Y10T 37/85994; Y10T 37/86493; Y10T 37/96549; Y10T 37/86863; Y10T 37/86871; F16K 3/00; F16K 3/22; F16K 3/24; F16K 3/26; F16K 3/262; F16K 5/00; F16K 5/04; F16K 5/0414; F16K 5/0442; F16K 11/00; F16K 11/02; F16K 11/06; F16K 11/065; F16K 11/07; F16K 11/0716; F16K 11/08; F16K 11/085; F16K 11/0853; F16K 11/0856
See application file for complete search history.

(56) References Cited

U.S. PATENT DOCUMENTS

| | | | |
|---|---|---|---|
| 4,365,943 | A | 12/1982 | Durrum |
| 4,493,706 | A | 1/1985 | Borsanyi et al. |
| 5,004,013 | A | 4/1991 | Beaston |
| 5,104,387 | A * | 4/1992 | Pokorney ............ F16K 11/0856 604/248 |
| 5,817,068 | A * | 10/1998 | Urrutia ............... F16K 11/0853 251/207 |
| 2001/0025942 | A1 | 10/2001 | Lotz et al. |
| 2006/0089603 | A1 | 4/2006 | Truitt et al. |
| 2010/0082016 | A1 | 4/2010 | Graham |
| 2010/0274179 | A1 | 10/2010 | Derichs |
| 2011/0071465 | A1 | 3/2011 | Wang |
| 2011/0282276 | A1 | 11/2011 | Abal |

FOREIGN PATENT DOCUMENTS

| | | |
|---|---|---|
| EP | 2168611 | 3/2010 |
| FR | 2358601 A1 | 2/1978 |
| GB | 117997 | 8/1918 |
| GB | 447938 | 5/1936 |
| JP | H0266957 | 5/1990 |
| JP | H0425751 | 2/1992 |
| JP | H11267204 | 10/1999 |
| JP | 2000237308 | 9/2000 |
| JP | 2004087911 | 3/2004 |
| JP | 2005524804 | 8/2005 |
| JP | 2007061389 | 3/2007 |
| JP | 2008517653 | 5/2008 |
| JP | 2010082456 | 4/2010 |
| WO | WO-2008/144622 | 11/2008 |
| WO | WO-2010/140063 | 12/2010 |
| WO | WO-2011008619 | 1/2011 |
| WO | WO-2011/148120 | 12/2011 |

OTHER PUBLICATIONS

Canada Office Action for Application No. 2875527, dated Feb. 28, 2020, 3 pages.
Canadian Office Action for Application No. 2875527, dated Apr. 15, 2019, 7 pages.
Canadian Office Action for Application No. 3098215, dated Dec. 24, 2021, 5 pages.
European Office Action for Application No. 13733131.0, dated Apr. 9, 2021, 4 pages.
European Office Action for Application No. 13733131.0, dated Feb. 21, 2018, 4 pages.
European Office Action for Application No. 13733131.0, dated Feb. 24, 2016, 5 pages.
European Office Action for Application No. 13733131.0, dated Oct. 28, 2021, 4 pages.
International Search Report and Written Opinion, dated Feb. 24, 2014, directed to corresponding International Patent Application No. PCT/US2013/044595, 14 pages in English language.
Japanese Office Action for Application No. 2015-517315, dated Mar. 1, 2017, 4 pages excluding English translation.
Japanese Office Action for Application No. 2015-517315, dated Nov. 1, 2017, 4 excluding translation.

* cited by examiner

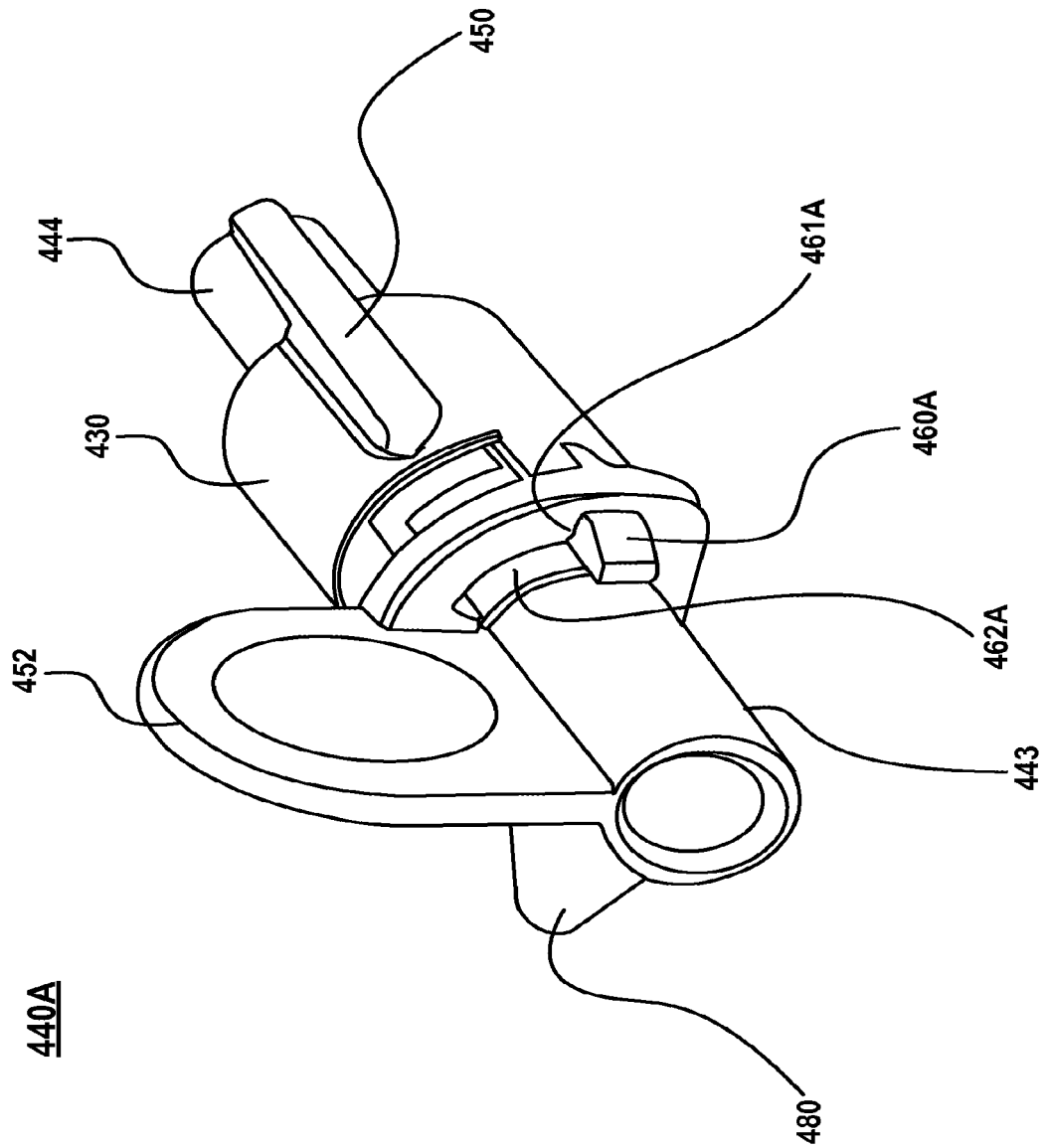

700

```
┌─────────────────────────────────────────────────────────────┐
│ ACTUATE A NON-PINCHING VALVE TO A CLOSED POSITION BY        │
│ ROTATING A SLIDABLE COVER AXIALLY OVER A HOUSING OF SAID    │
│ NON-PINCHING VALVE, WHEREIN THE NON-PINCHING VALVE          │
│ CONTROLS FLOW OF A FLUID WITHOUT REQUIRING PINCHING         │
│ OF A TUBE ATTACHED TO THE NON-PINCHING VALVE                │
│                         710                                 │
└─────────────────────────────────────────────────────────────┘
                              │
                              ▼
┌─────────────────────────────────────────────────────────────┐
│   PLACE THE NON-PINCHING VALVE IN A HOUSING OF AN INFUSION PUMP │
│                         720                                 │
└─────────────────────────────────────────────────────────────┘
                              │
                              ▼
┌─────────────────────────────────────────────────────────────┐
│     CLOSE A DOOR OF THE INFUSION PUMP TO CLOSE ACCESS IN THE│
│                          HOUSING                            │
│                           730                               │
└─────────────────────────────────────────────────────────────┘
                              │
                              ▼
┌─────────────────────────────────────────────────────────────┐
│    IN RESPONSE TO THE CLOSING OF THE DOOR, ACTUATE THE      │
│   NON-PINCHING VALVE TO AN OPEN POSITION, BY THE DOOR, SUCH │
│       THAT FLUID FLOWS THROUGH THE NON-PINCHING VALVE       │
│                           740                               │
└─────────────────────────────────────────────────────────────┘

┌─────────────────────────────────────────────────────────────┐
│         FLUIDLY CONNECT THE NON-PINCHING VALVE TO AN IV     │
│                           750                               │
└─────────────────────────────────────────────────────────────┘

┌─────────────────────────────────────────────────────────────┐
│       FLUIDLY CONNECT THE NON-PINCHING VALVE TO A PATIENT   │
│                           760                               │
└─────────────────────────────────────────────────────────────┘
```

FIG. 7

FLUID FLOW CONTROL BY A NON-PINCHING VALVE

CROSS-REFERENCE TO RELATED APPLICATIONS

This application is a continuation of U.S. patent application Ser. No. 16/428,264, filed on May 31, 2019, which issued as U.S. Pat. No. 11,642,510 on May 9, 2023, entitled "FLUID FLOW CONTROL BY A NON-PINCHING VALVE," which is a divisional of U.S. patent application Ser. No. 13/525,205, filed on Jun. 15, 2012, which issued as U.S. Pat. No. 10,350,402 on Jul. 16, 2019, entitled "FLUID FLOW CONTROL BY A NON-PINCHING VALVE," the entire contents of which are incorporated by reference herein.

BACKGROUND

Controlling the fluid flow of a medical pump system, such as an infusion pump, by a clamping an intravenous (IV) tube can deleterious affect operation of the medical pump system. Clamping mechanisms, such as a roller clamp, screw clamp, slide clamp, compress a tube to control the fluid flow. For example, the slide clamp has a graduated opening through which the tube passes. Pushing the tube into the narrow end of the opening compresses the tube and reduces the flow rate of the fluid flow through the tube. In contrast, sliding towards the wide end of the opening decreases the compression of the tube and thus, increases the flow rate through the tube. Also, the tube may be shipped and/or stored for long periods of time with the clamping mechanism continually applying pressure to the tube.

As a result of the compression of the tube, the tube may be damaged and/or deformed. For example, the tube is permanently deformed and thus, restricts fluid flow.

Moreover, clinicians may improperly insert/remove components from the pump housing. For example, it may be difficult for the clinician to visually determine where certain components (e.g., clamping device, pumping segment, etc.) are to be placed within the pump housing. As a result, the clinician may place the components in the wrong position which negatively affects the pumping operation.

SUMMARY

In one or more embodiments, a non-pinching valve includes a housing having a first port disposed on a first side of the housing and a second port disposed on an opposing second side of the housing, a shaft, a channel and a handle coupled to the shaft. When the shaft is disposed in a first position, the channel is aligned with the first port and the second port, the channel configured to allow fluid to flow between the first port and the second port. When the shaft is disposed in a second position, the channel is not aligned with the first port and the second port and the shaft is configured to block fluid flow between the first port and the second port.

In one or more embodiments, a pump system includes a pump configured for pumping a fluid in a medical environment, a tube configured for conveyance of the fluid and a non-pinching valve releasably attached to the tube, the non-pinching valve configured to be disposed in a pump housing and to control a flow of the fluid without requiring pinching of the tube. The tube is releasably attached to the non-pinching valve. The non-pinching valve includes a housing having a first port disposed on a first side of the housing and a second port disposed on an opposing second side of the housing, a shaft, a channel and a handle coupled to the shaft, wherein when the shaft is disposed in a first position, the channel is aligned with the first port and the second port, the channel configured to allow fluid to flow between the first port and the second port, and wherein when the shaft is disposed in a second position, the channel is not aligned with the first port and the second port and the shaft is configured to block fluid flow between the first port and the second port.

Additional features and advantages of the disclosure will be set forth in the description below and, in part, will be apparent from the description or may be learned by practice of the disclosure. The objectives and other advantages of the disclosure will be realized and attained by the structure particularly pointed out in the written description and claims hereof as well as the appended drawings.

It is to be understood that both the foregoing general description and the following detailed description are exemplary and explanatory and are intended to provide further explanation of the disclosure as claimed.

BRIEF DESCRIPTION OF THE DRAWINGS

FIG. 7 illustrates an embodiment of a method for controlling fluid flow.

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, components, and circuits have not been described in detail as not to unnecessarily obscure aspects of the present embodiments.

Figure 1A:
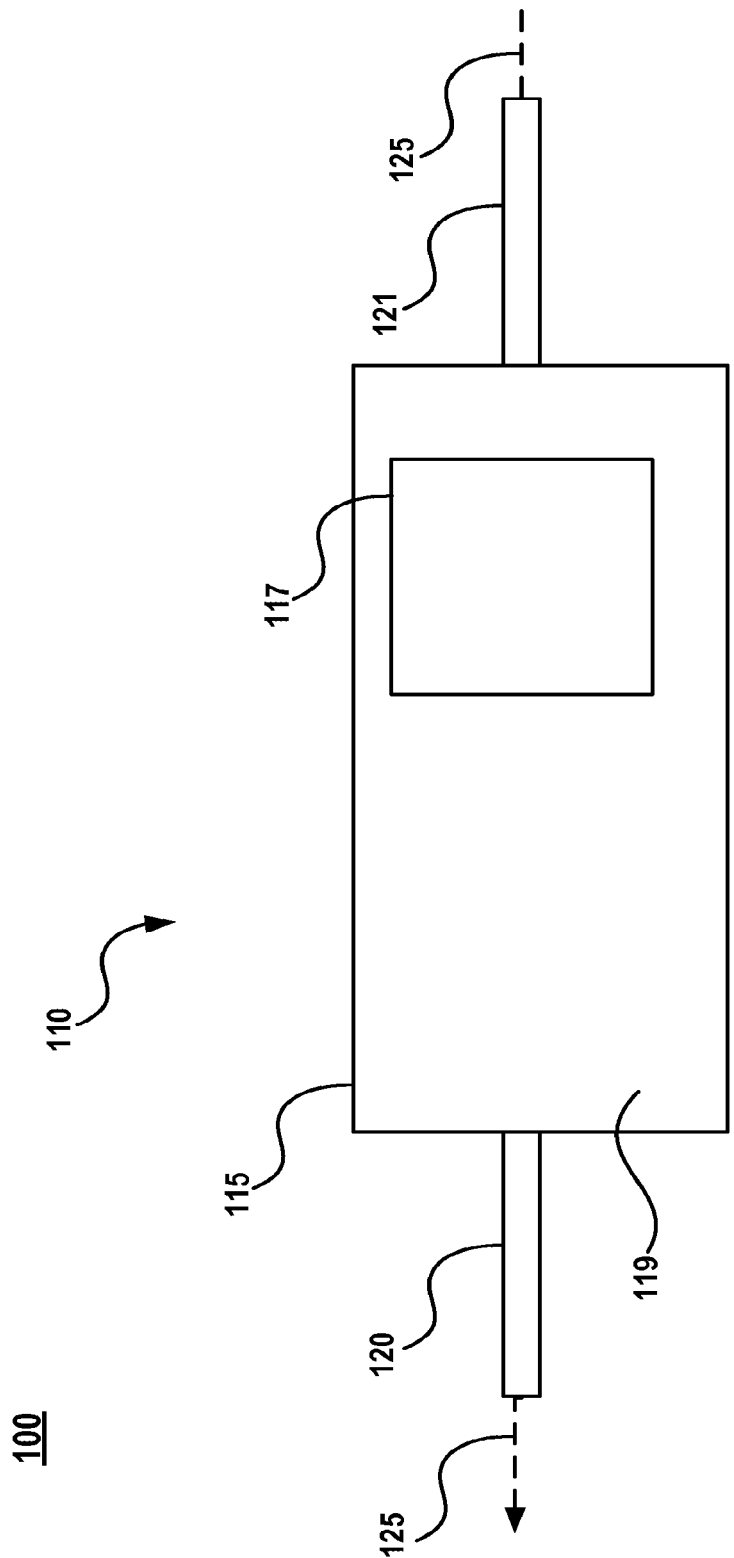
FIGS. 1A-B illustrates embodiments of a pumping system.

FIG. 1A depicts an embodiment of pumping system 100. Pumping system 100 includes pump 10 and tubes 120 and 121. In general, during operation of pumping system 100, fluid is pumped through tubes 120 and 121 as indicated by fluid flow 125. In one embodiment, fluid flow 125 may be pumped in the opposite direction.

Pump 110 includes housing 115, door 119 and user interface 117. In one embodiment, pump 110 is an infusion pump. For example, fluid from an intravenous (IV) bag (not shown) is pumped to a patient (not shown) as indicted by fluid flow 125.

User interface 117 can include a display, buttons, controls, etc. for use by a clinician to facilitate in control of pumping system 100.

Housing 115 is configured to hold the components of pump 110, as will be described in detail below.

Door 119 is removable or hinged with respect to housing 115. For example, door 119 is the entire front face of pump 110 and is removable from housing 115 to provide access within housing 115. It should be understood that door 119 (or lid) can be any dimension, shape, orientation that enables access for proper placement and/or removal of components from within housing 115.

Figure 1B:
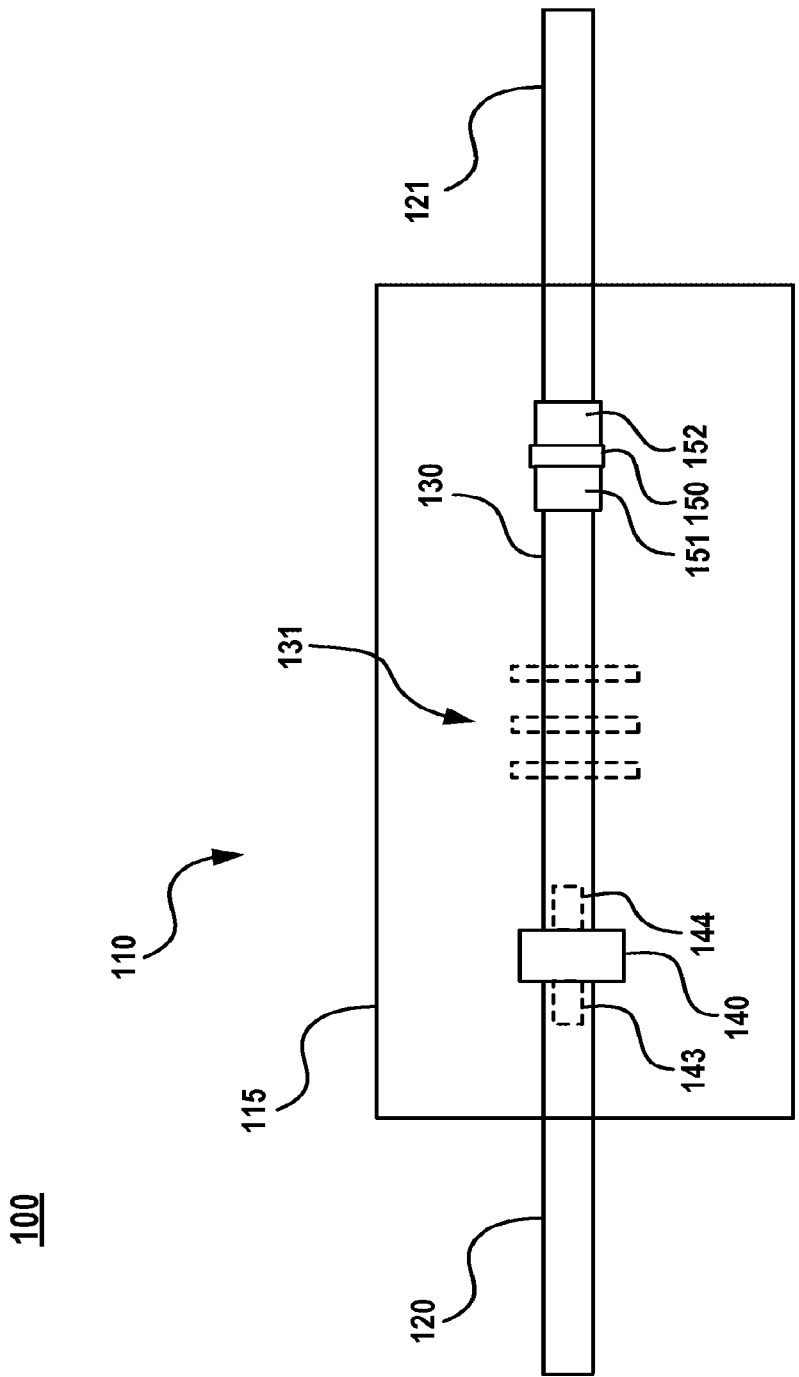

FIG. 1B depicts an embodiment of pumping system 100. In particular, FIG. 1B depicts the same view as FIG. 1A, however, door 119 is not shown. Accordingly, components of pump 110 within housing 115 are depicted.

Pump 110 also includes pumping segment 130, pumping fingers 131, non-pinching valve 140, and coupler 150.

Pumping segment 130 is configured to be easily compressed by fingers 131. For example, pumping segment 130 is a silicone rubber tube.

In one embodiment, tubes 120 and 121 are comprised of the same material and pumping segment is comprised of a more pliable material, such as silicone. It should be understood that pumping segment 130 can be any material that is conducive to being compressed by fingers 131.

Pumping segment 130 is fluidly connected to tube 120 via non-pinching valve 140 and fluidly connected to tube 121 via coupler 150. For example, in one embodiment, outer diameter of tube 121 mates with the inner diameter of interface 152. Similarly, the outer diameter of segment 130 mates with the inner diameter of interface 151. In another embodiment, the inner diameter of pumping segment 130 mates with the outer diameter of interface 144. Similarly, the inner diameter of tube 120 mates with the outer diameter of interface 143. It should be understood that pumping segment 130 can be fluidly connected to tubes 120 and 121 by any coupling means.

In one embodiment, coupler 150 is a "Y" coupler that accommodates two different tubes (e.g., tube 121 and another tube (not shown)). For example, tube 121 conveys a first type of fluid (e.g., a first type of medicine) and the other tube conveys a second type of fluid (e.g., a second type of medicine). Accordingly, the different types of fluid may mix at coupler 150 and the mixture of fluid is pumped by pumping system 100.

Pumping fingers 131 are configured to compress pumping segment 130 to pump fluid. For example, fingers 131 press on pumping segment 130 in sequence. In particular, fingers 131 compress pumping segment 130 against a platen (not shown). As a result, fluid flow 125 is generated.

Non-pinching valve 140 is configured to control fluid flow 125 in pumping system 100 without requiring pinching of a tube (e.g. 120). In other words, non-pinching valve 140 controls fluid flow 125 without applying pressure to an outer surface of a tube and thereby not compressing the tube. In one embodiment, non-pinching valve 140 is a stop cock. Non-pinching valve 140 can be any valving system that controls fluid flow 125 without compressing a tube. It should be appreciated that non-pinching valve 140 and a connected tube (e.g., tube 120) can be shipped and/or stored in the closed or open position without damaging the tube.

Figure 2A:
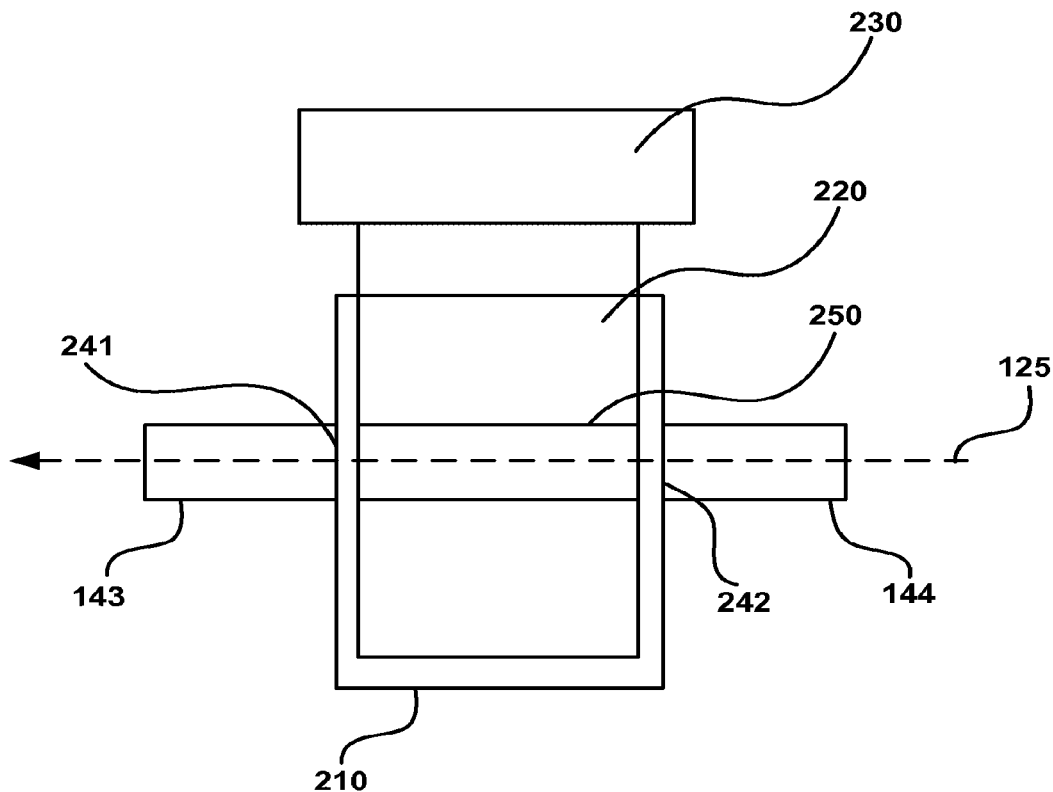
FIGS. 2A-4C illustrates embodiments of a non-pinching valve.

FIG. 2A depicts an embodiment of non-pinching valve 240A. Non-pinching valve 240A includes housing 210, ports 241 and 242 of housing 210, shaft 220, channel 250 and handle 230. Ports 241 and 242 are a hole or access point for fluid with respect to housing 210.

In general, when channel 250 is aligned with ports 241 and 242, fluid flow 125 flows through channel 250 and subsequently through non-pinching valve 240A. In contrast, when channel 250 is not aligned with ports 241 and 242, fluid flow 125 does not flow through channel 250 and thus, not through non-pinching valve 240A.

In one embodiment, housing 210 and shaft 220 are cylindrical. For example, fluid flow 125 is stopped when channel 250 is not aligned with ports 241 and 242. In such an example, a clinician rotates handle 230 (e.g., 90 degrees from the depicted position) such that channel 250 is not aligned with ports 241 and 242. Accordingly, shaft 220 seals ports 242 and 241 such that fluid flow is stopped and does not flow through channel 250.

It should be understood that channel 250 rotates perpendicularly to the direction of fluid flow 125. Moreover, interfaces 143 and 144 and channel 250 are coaxial or collinear with one another. Accordingly, fluid flow 125 can occur in two discrete positions of shaft 220. The first position, is as depicted. The second position is shaft 220 rotated 180 degrees (from the depicted position).

In one embodiment, the cross-sectional shape (e.g. circular) and diameter of ports 241 and 242, and channel 250 are the same. In another embodiment, the cross-sectional shape of channel 250 is different (e.g., oval, tear drop, etc.) than the cross-sectional shape of ports 241 and 242 to facilitate in manual regulation of fluid flow 125.

In various embodiments, housing 210 and shaft 220 are comprised of a rigid or semi-rigid material.

Figure 2B:
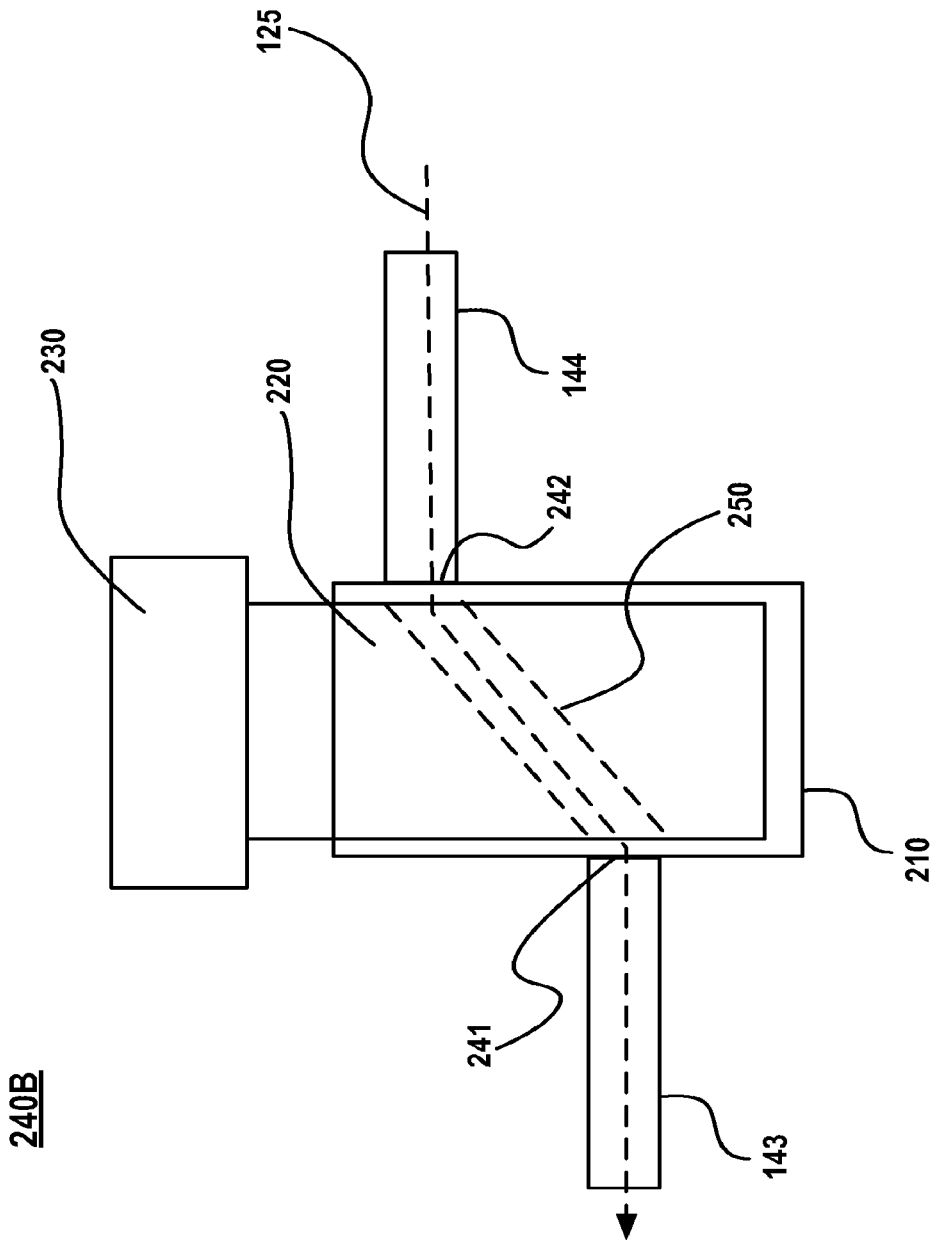

FIG. 2B depicts an embodiment of non-pinching valve 240B. Non-pinching valve 240B is similar to non-pinching valve 240A, as described above. However, ports 241 and 242 are not coaxial and channel 250 is disposed at an angle within shaft 220.

Accordingly, in one embodiment, channel 250 is aligned with ports 241 and 242 at one position. For example, if shaft 220 is rotated to any other position (other than the depicted position), then fluid does not flow through channel 250.

Figure 2C:
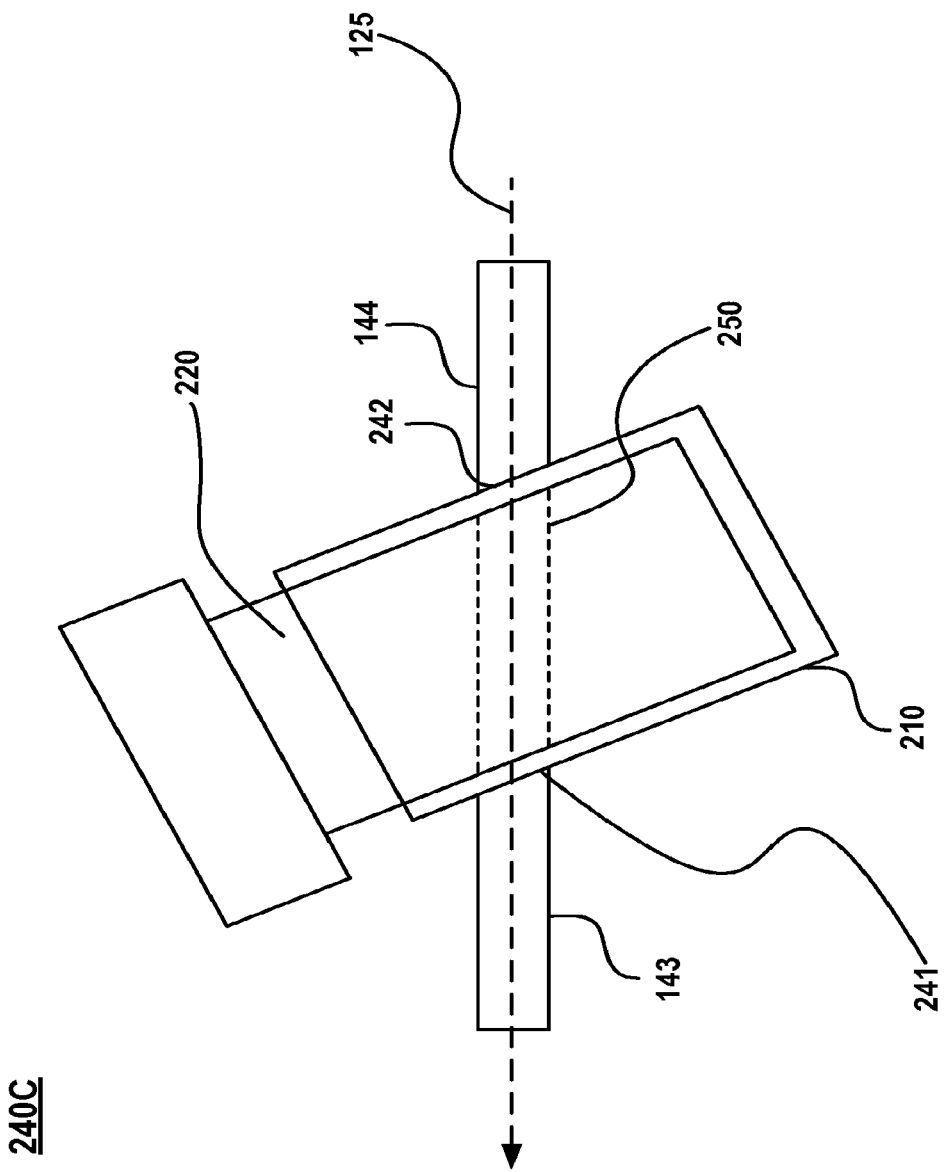

FIG. 2C depicts an embodiment of non-pinching valve 240C. Non-pinching valve 240C is similar to non-pinching valve 240A, as described above. However, housing 210 is disposed at an angle with respect to fluid flow 125.

Accordingly, in one embodiment, channel 250 is aligned with ports 241 and 242 at a single position. For example, if shaft 220 is rotated to any other position (other than the depicted position), then fluid does not flow through channel 250.

Figure 2D:
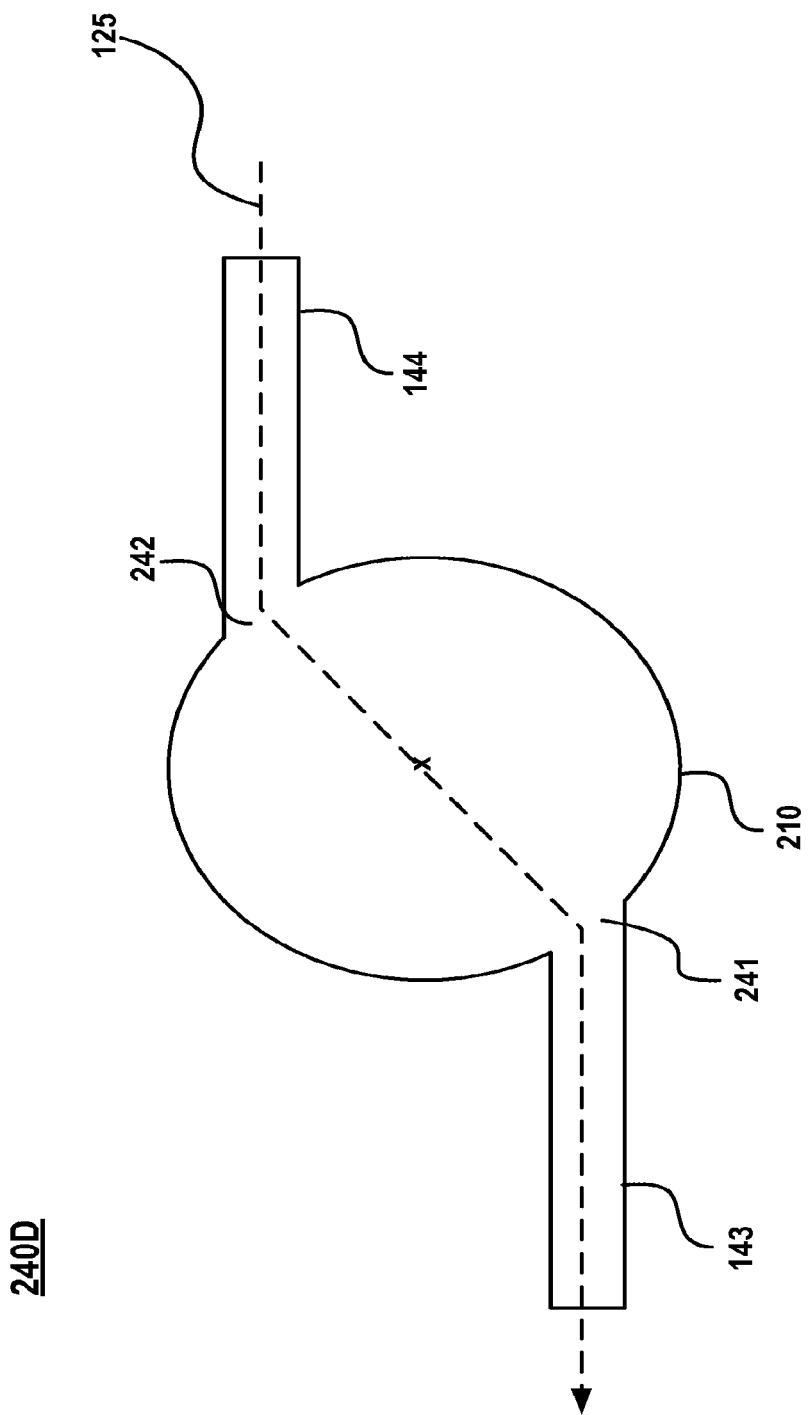

FIG. 2D depicts an embodiment of non-pinching valve 2400. Non-pinching valve 2400 is similar to non-pinching valve 240A, as described above. However, ports 241 and 242 are not coaxial with one another.

Figure 2E:
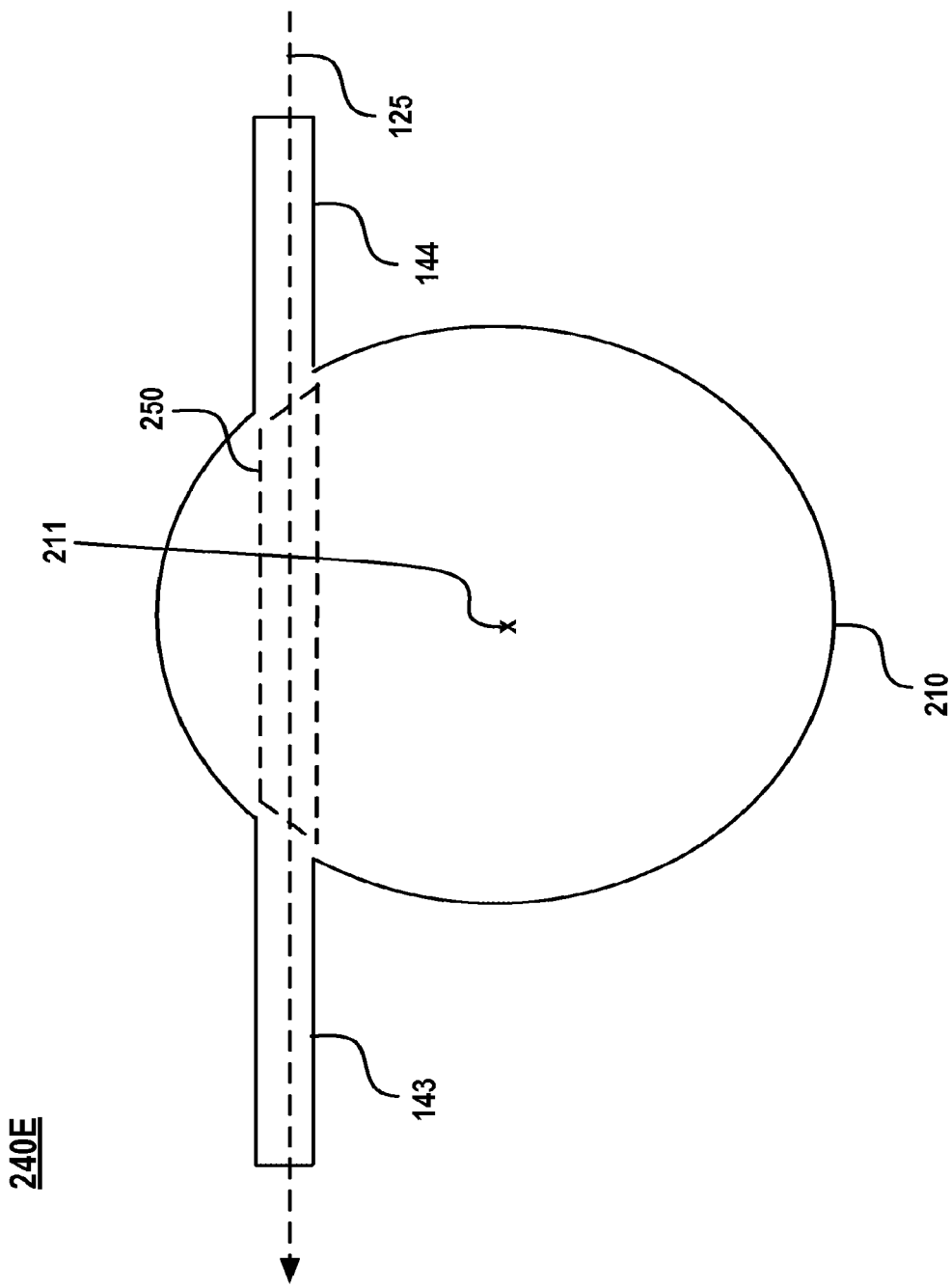

FIG. 2E depicts an embodiment of non-pinching valve 240E. Non-pinching valve 240E is similar to non-pinching valve 240A, as described above. However, fluid flow 125 does not flow through the axis of housing 210 (or shaft 220).

Figure 3A:
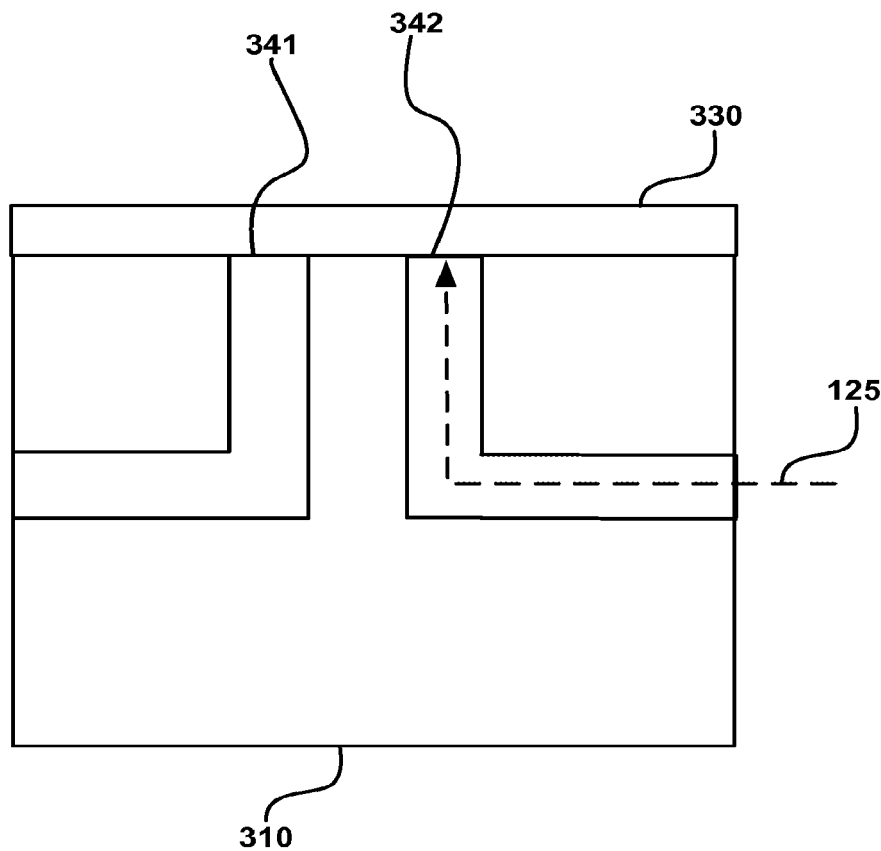
Figure 3B:
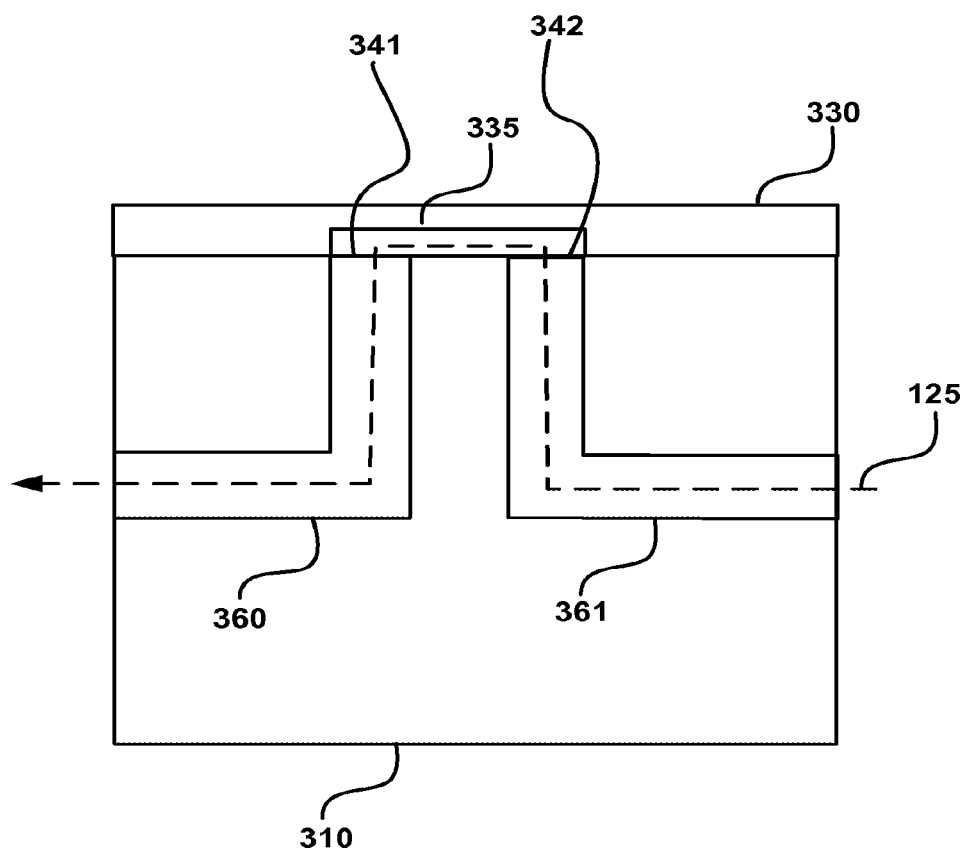

FIGS. 3A-B depicts an embodiment of non-pinching valve 340. Non-pinching valve 340 includes housing 310, ports 341 and 342, and slidable cover 330. In various embodiments, housing 310 and slidable cover 330 are comprised of a rigid or semi-rigid material.

Slidable cover 330 is configured to slide with respect to housing 310 to control fluid flow 125. Slidable cover 330 includes channel 335.

FIG. 3A depicts non-pinching valve 340 in a closed position. For example, slidable cover 330 seals ports 341 and 342 such that fluid flow 125 cannot flow through non-pinching valve 340.

FIG. 3B depicts non-pinching valve 340 in an open position. For example, slidable channel 335 is aligned with ports 341 and 342. Accordingly, fluid flow 125 flows through non-pinching valve 340 via channel 335. It should be appreciated that channel 335 can be any feature in any location or orientation on slidable cover 330 (e.g., void, hallow, groove, etc.) that is able to convey water between ports 341 and 342.

In particular, fluid flow 125 occurs between housing 310 and slidable cover 330 via channel 335. As such, fluid flow 125 flows along the outer surface or periphery of housing 310.

In one embodiment, housing 310 and slidable cover 330 are cylindrical.

In another embodiment, channels 360 and 361 are disposed along the center axis of housing 310. Accordingly, slidable cover 330 slides axially with respect to housing 310 and channels 360 and 361. Also, slidable cover 330 slides axially with respect to portions of fluid flow 125.

Figure 4B:
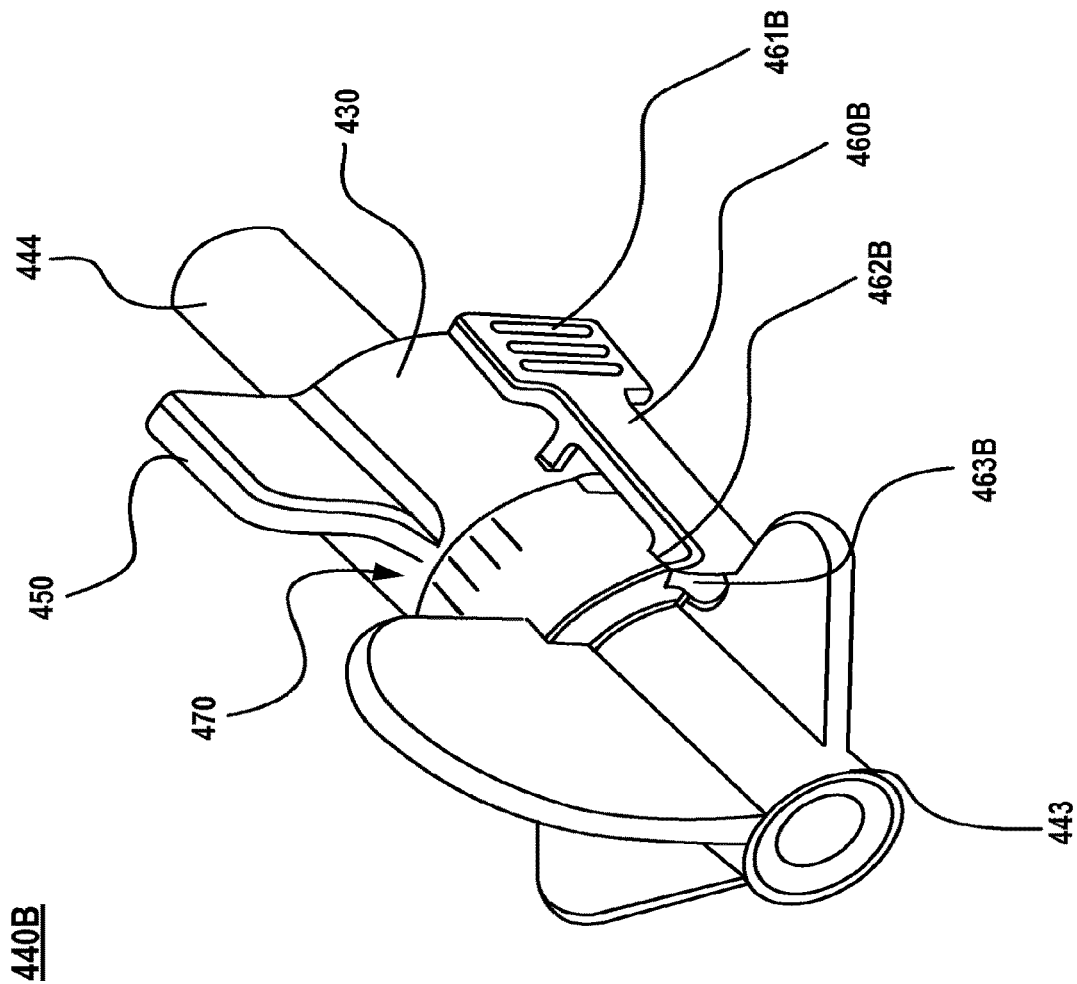
Figure 4C:
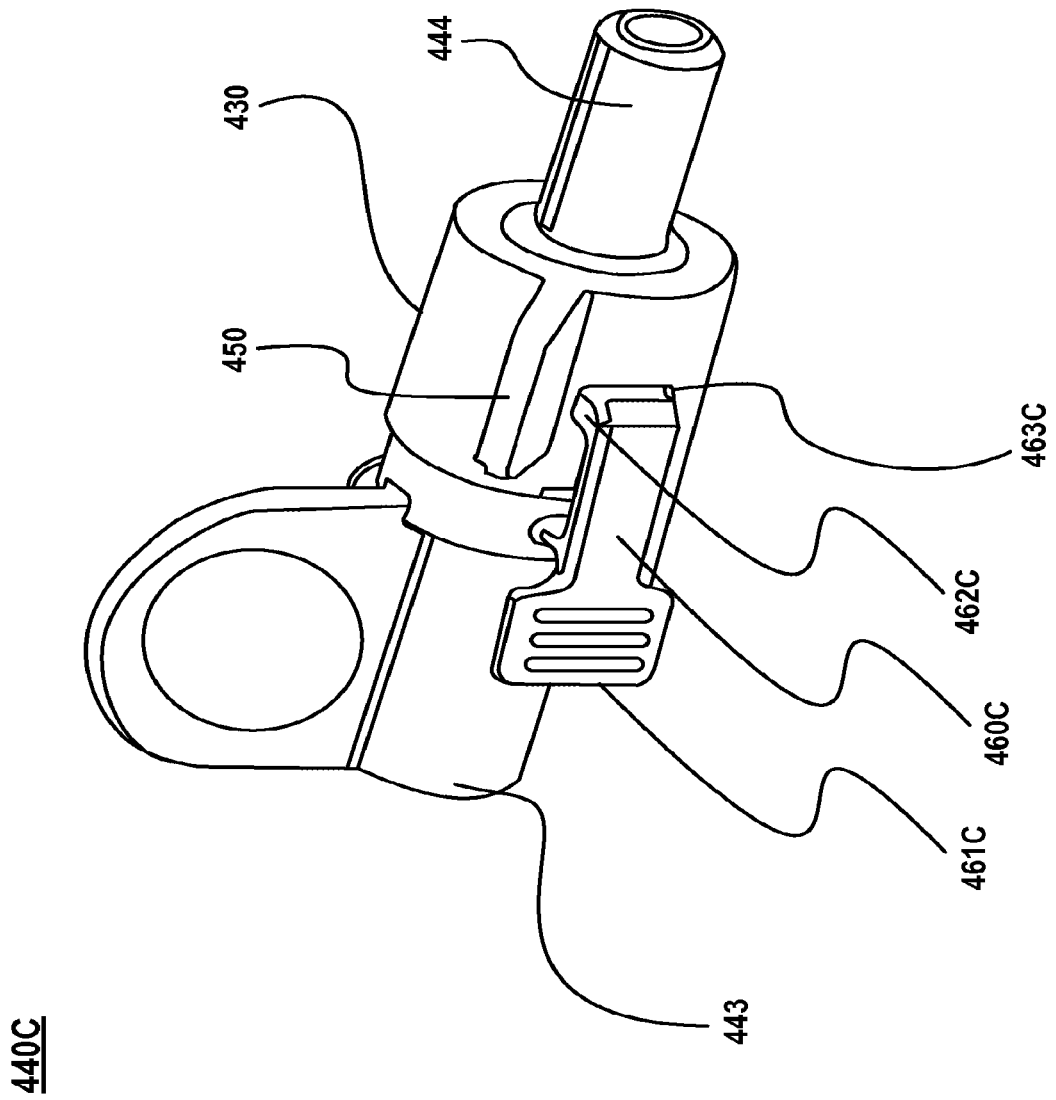

FIGS. 4A-C depicts embodiments of non-pinching valves 440A-C, respectively. Non-pinching valves 440A-C are similar to non-pinching valve 340, as described above. However, among other things, non-pinching valves 440A-C each include a locking mechanism.

Referring now to FIG. 4A, non-pinching valve 440A includes slidable cover 430, interfaces 443 and 444, handles 450 and 452, visual indicator 480 and locking mechanism 460A.

Interfaces 443 and 444 are configured to couple tubes to non-pinching valve 440A.

Handle 450 facilitates in rotating slidable cover 430 along an axis of non-pinching valve 440A.

Handle 452 facilitates a clinician in placing or seating non-pinching valve 440A into housing 115. For example, a clinician grasps handle 452 while placing non-pinching valve 440A into housing 115 or removing non-pinching valve 440A from housing 115.

Visual indicator 480 is configured to facilitate a clinician in properly placing non-pinching valve 440A in housing 115, which will be described in detail below.

Locking mechanism 460A is a tab that is seated in slot 461A such that non-pinching valve 440A is locked in either an open or closed position (or any other designated position, such as one half flow rate). In order to unlock non-pinching valve 440A, locking mechanism 460A is pushed out of slot 461 such that it is able to travel along slot 462A.

Referring now to FIG. 4B, locking mechanism 460B comprises tab 462B that is seated in slot 463B such that non-pinching valve 440B is locked in either an open or closed position. In order to unlock non-pinching valve 440B, depresser 461 B is depressed such that tab 462B is pulled away from slot 463B.

Non-pinching valve 440B also includes graduation markings 470. Each graduation marking is indicative of a particular flow rate. Accordingly, graduation markings facilitate in controlling the flow rate through non-pinching valve 440B. In a further embodiment, graduation markings 470 are coupled with a tactile and/or audible indication. For example, when the non-pinching valve is actuated according to the graduation markings, the clinician may feel a tactile response and/or an audible response, such as a click.

Referring now to FIG. 4C, locking mechanism 460C comprises tab 462C that is seated in slot 463C such that non-pinching valve 440C is locked in either an open or closed position. In order to unlock non-pinching valve 440B, de presser 461 C is depressed such that tab 462C is pulled away from slot 463C.

In various embodiments, a non-pinching valve (e.g., non-pinching valve 240A) is actuated to an open position in response to the closing of door 119. In particular, door 119 comprises an engagement feature (not shown) that mechanically engages with a handle (e.g., handle 230). For example, the engagement feature has particular beveled features that engage with the handle and actuate the handle, such that the non-pinching valve is actuated from the closed position to the open position, when door 119 is pressed into place.

In another embodiment, a non-pinching valve (e.g., non-pinching valve 240A) is actuated to a closed position in response to the opening of door 119. In particular, door 119 comprises an engagement feature (not shown) that mechanically engages with a handle (e.g., handle 230). For example, the engagement feature mechanically engages with the handle, such that the non-pinching valve is actuated from the open position to the closed position, when door 119 is opened or removed from housing 115.

It should be appreciated that a non-pinching valve can be utilized without the use of a pump. For example, in a gravity fed fluid flow system, the non-pinching valve can be utilized to control flow of fluid to a patient.

Figure 5:
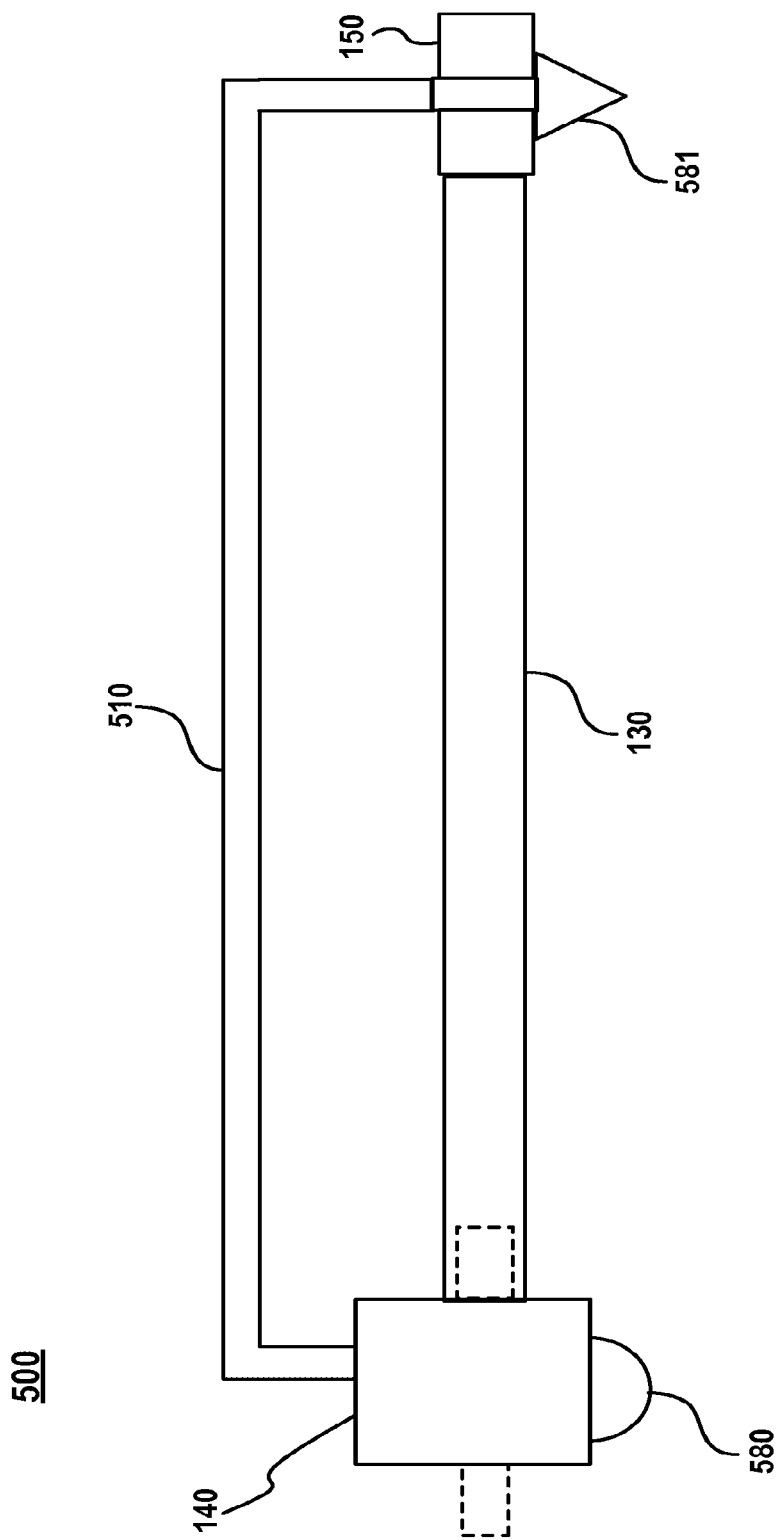
FIGS. 5 and 6 illustrates embodiments of a pump segment frame system.

FIG. 5 depicts an embodiment of pump segment frame system 500. System 500 includes non-pinching valve 140, coupler 150 and pumping segment 130.

Frame 510 is configured to prevent pumping segment 130 from stretching.

In particular, distal ends of pumping segment 130 are attached to corresponding distal ends of frame 510, which is comprised of a rigid or semi-rigid material. Accordingly, pumping segment 130 is prevented from stretching.

In contrast, in a conventional system, if a pumping segment is stretched, for example when a clinician places the pumping segment in the housing, then the pumping segment is likely to be improperly placed in the housing. As a result, the operation of the pumping system is negatively affected.

In one embodiment, non-pinching valve 140 is disposed at a distal end of frame 510. As such, a distal end of pumping segment 130 is attached to non-pinching valve 140.

In another embodiment, coupler 150 is attached to a distal end of frame 510. As such, a distal end of pumping segment 130 is attached to coupler 150.

System 500 also includes visual indicators 580 and 581. In general, visual indicators 580 and 581 facilitate in the proper placement of system 500 into housing 115. For example, housing 115 includes visual indicators corresponding to visual indicators 580 and 581. The corresponding visual indicators in housing 115 can be an outline, indention, etc. that corresponds to visual indicators 580 and 581. As a result, system 500 is properly placed in housing 115 such that pumping system 100 operates correctly.

In various embodiments, the corresponding visual indicators in housing 115 can be a color or an outline of components (e.g., outline of non-pinching valve 140, frame 510, coupler 150, etc.).

Figure 6:
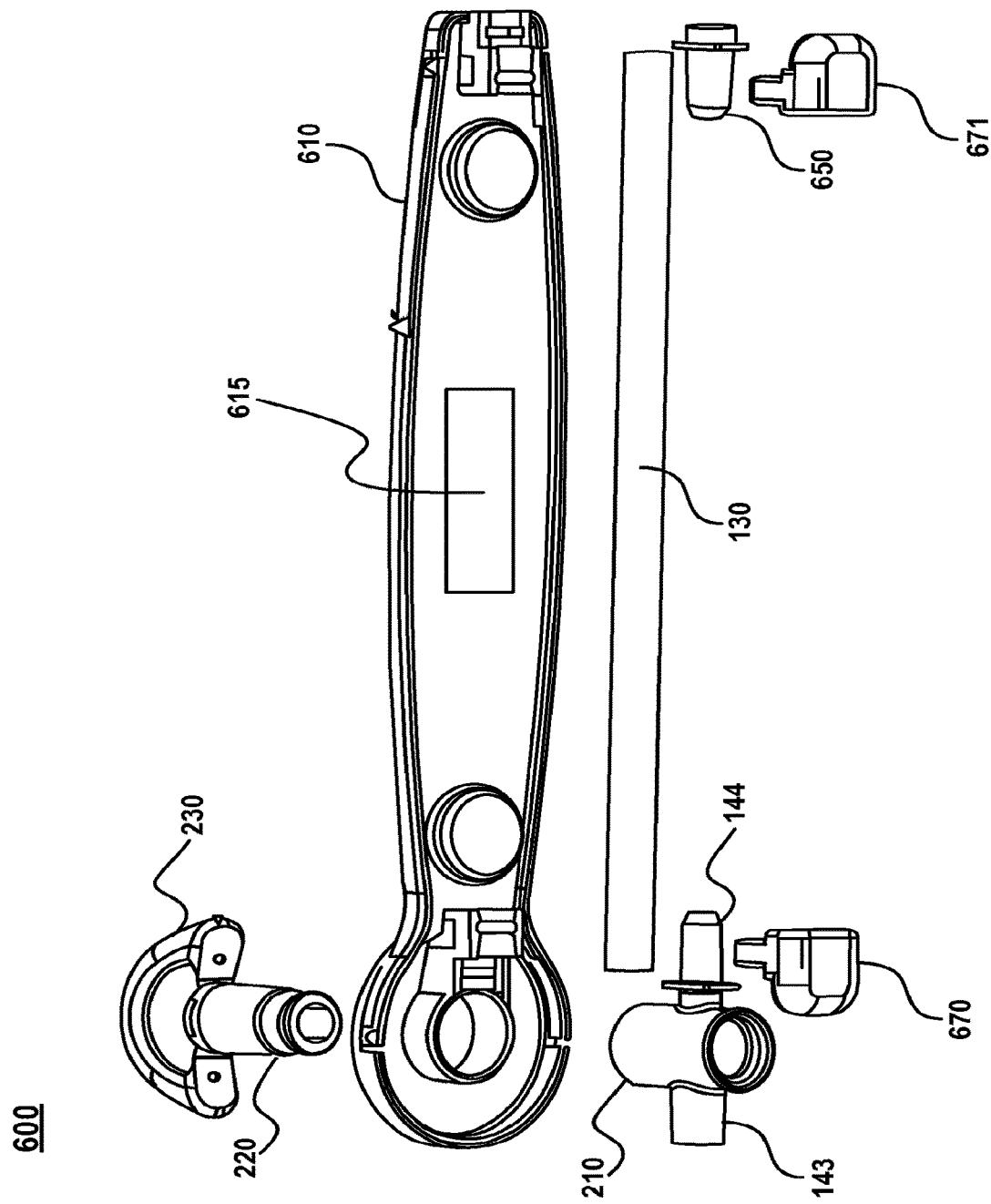

FIG. 6 depicts an exploded isometric view of an embodiment of pump segment frame system 600. System 600 includes non-pinching valve 140, coupler 650 and pumping segment 130.

Frame 610 is configured to prevent pumping segment 130 from stretching, as described above. For example, distal ends of pumping segment 130 are attached to corresponding distal ends of frame 610, which is comprised of a rigid or semi-rigid material. Accordingly, pumping segment 130 is prevented from stretching.

Frame 610 is further configured to be a platen. For example, fingers 131 extend within housing 115 and compress pumping segment 130 against frame 610. Moreover, the placement of pumping segment 130 with respect to frame 610 provides a consistent gap (e.g., between pumping segment 130 and frame 610) to facilitate in pumping and pressure sensing.

In one embodiment, frame 610 includes a window such that pumping segment 130 is viewable during use of pumping system 100.

In one embodiment, a non-pinching valve (e.g., non-pinching valve 240A) is disposed at a distal end of frame 610. As such, a distal end of pumping segment 130 is attached to the non-pinching valve. In such an embodiment, frame 610 is interposed between housing 210 and handle 230.

In another embodiment, coupler 650 is attached to a distal end of frame 610. As such, a distal end of pumping segment 130 is attached to coupler 671.

System 600 also includes retainers 670 and 671 that facilitate in retaining pumping segment 130 on housing 210 and coupler 650. In particular, retainers 670 and 671 clamp the distal ends of pumping segment 130 on interface 144 and coupler 650.

It should be understood that pumping segment 130 may be replaced with another pumping segment. In some instances, characteristics (e.g., diameter, material, etc.) of the new pumping segment may be different than the pumping segment that is replaced. To accommodate the characteristics of the pumping segment, the gap between the platen (e.g., frame 610) or pressure sensors and the pumping fingers may be required to be adjusted. Accordingly, in convention pumping systems, the hardware/software of the pumping system may be required to be upgraded to accommodate the new characteristics of the new pumping segment.

However, in various embodiments, the thickness of frame 610 is adjustable. That is, frame 610 of one thickness can be swapped out with a frame of a different thickness to accommodate the characteristics of the new pumping segment. In one embodiment, the new frame has a different thickness (than the original frame) to accommodate for the change in the gap between the platen (e.g., frame 610) or pressure sensors and the pumping fingers. Therefore, the hardware/software of the pumping system is not required to be updated in response to replacing pumping segment 130 with another pumping segment with different characteristics.

FIG. 7 depicts an embodiment of a method 700 for controlling fluid flow. In some embodiments, method 700 is performed at least by system 100, as depicted in FIG. 1A.

At 710 of method 700, a non-pinching valve is actuated to a closed position by rotating a slidable cover axially over a housing of said non-pinching valve, wherein the non-pinching valve controls flow of a fluid without requiring pinching of a tube attached to the non-pinching valve. For example, non-pinching valve 340 is initially actuated manually to a closed position such fluid does flow through system 100. In particular, slidable cover 330 is manually axially rotated over housing 310 of non-pinching valve 340. Accordingly, non-pinching valve 340 is able to control flow through system 100 without requiring to pinch a tube (e.g., tube 120) that is attached to the valve.

At 720, the non-pinching valve is placed in a housing of an infusion pump. For example, non-pinching valve 240A is placed in housing 115 of an infusion pump.

At 730, a door of the infusion pump to close access in the housing. For example, door 119 is placed over housing 115 to restrict access housing 115.

At 740, in response to the closing of the door, the non-pinching valve is actuated to an open position, by the door, such that fluid flows through the non-pinching valve. For example, handle 230 is actuated by a feature of door 119 such that fluid flow 125 flows through non-pinching valve 240A.

In one embodiment, at 750, the non-pinching valve is fluidly connected to an IV. For example, non-pinching valve 440B is fluidly connected to an IV such that a fluid in the IV bag is able to be pumped to a patient.

In one embodiment, at 760, the non-pinching valve is fluidly connected to a patient. For example, non-pinching valve 440B is fluidly connected to a patient (not shown) such that a fluid in the IV bag is able to be pumped to a patient via system 100.

Various embodiments of the present invention are thus described. It should be appreciated that embodiments, as described herein, can be utilized or implemented alone or in combination with one another. While the present invention has been described in particular embodiments, it should be appreciated that the present invention should not be construed as limited by such embodiments, but rather construed according to the following claims.

The invention claimed is:

1. A non-pinching valve comprising:
a housing having a first port disposed on a first side of the housing and a second port disposed on an opposing second side of the housing;
a shaft;
a channel; and
a handle coupled to the shaft,
wherein when the shaft is disposed in a first position, the channel is aligned with the first port and the second port, the channel configured to allow a fluid to flow between the first port and the second port,
wherein when the shaft is disposed in a second position, the channel is not aligned with the first port and the second port and the shaft is configured to block the flow of the fluid between the first port and the second port,
wherein the channel has a different perimeter cross-sectional shape than a perimeter cross-sectional shape of the first port and the second port, wherein the different perimeter cross-sectional shape of the channel is a tear drop shape.

2. The non-pinching valve of claim 1, wherein the housing and the shaft are cylindrical.

3. The non-pinching valve of claim 2, wherein the second position of the shaft is disposed at ninety degrees of axial rotation from the first position of the shaft.

4. The non-pinching valve of claim 2, wherein a third position of the shaft is disposed at one hundred eighty degrees of axial rotation from the first position of the shaft, wherein when the shaft is disposed in the third position, the channel is aligned with the first port and the second port, the channel configured to allow the fluid to flow between the first port and the second port.

5. The non-pinching valve of claim 1, further comprising:
a first tube interface extending perpendicularly from the first side of the housing, the first tube interface coupled to the first port; and
a second tube interface extending perpendicularly from the second side of the housing, the second tube interface coupled to the second port.

6. The non-pinching valve of claim 5, wherein the channel, the first tube interface and the second tube interface are collinear with one another.

7. The non-pinching valve of claim 1, wherein the perimeter cross-sectional shape of the first port and the second port is circular.

8. The non-pinching valve of claim 1, wherein the first port and the second port are not coaxial with one another, and wherein the channel is disposed at an angle within the shaft.

9. The non-pinching valve of claim 8, wherein the first position of the shaft is the only position of the shaft configured to allow the fluid to flow between the first port and the second port, and wherein the second position of the shaft is any rotational position of the shaft other than the first position.

10. The non-pinching valve of claim 8, further comprising:
   a first tube interface extending at a perpendicular angle from the first side of the housing, the first tube interface coupled to the first port; and
   a second tube interface extending at a perpendicular angle from the second side of the housing, the second tube interface coupled to the second port.

11. The non-pinching valve of claim 10, wherein when the shaft is disposed in the first position, the first port and the first tube interface are parallel but not coaxial to the second port and the second tube interface, and wherein a first end of the angled channel is aligned with the first port and a second end of the angled channel is aligned with the second port.

12. The non-pinching valve of claim 8, further comprising:
   a first tube interface extending at a non-perpendicular angle from the first side of the housing, the first tube interface coupled to the first port; and
   a second tube interface extending at a non-perpendicular angle from the second side of the housing, the second tube interface coupled to the second port.

13. The non-pinching valve of claim 12, wherein when the shaft is disposed in the first position, a first end of the angled channel is aligned with the first port and the first tube interface and a second end of the angled channel is aligned with the second port and the second tube interface.

14. A pump system comprising:
   a pump configured for pumping a fluid in a medical environment;
   a tube configured for conveyance of the fluid; and
   a non-pinching valve releasably attached to the tube, the non-pinching valve configured to be disposed in a pump housing and to control a flow of the fluid without requiring pinching of the tube, the non-pinching valve comprising:
      a housing having a first port disposed on a first side of the housing and a second port disposed on an opposing second side of the housing;
      a shaft;
      a channel, wherein the channel has a different perimeter cross-sectional shape than a perimeter cross-sectional shape of the first port and the second port, wherein the different perimeter cross-sectional shape of the channel is a tear drop shape; and
      a handle coupled to the shaft,
      wherein when the shaft is disposed in a first position, the channel is aligned with the first port and the second port, the channel configured to allow the fluid to flow between the first port and the second port,
      wherein when the shaft is disposed in a second position, the channel is not aligned with the first port and the second port and the shaft is configured to block fluid the flow of the fluid between the first port and the second port,
   wherein the pump comprises a door for access within the pump housing, and
   wherein the non-pinching valve is configured to be actuated into a closed position when the door of the pump is in an open position.

15. The pump system of claim 14, wherein the pump is an infusion pump.

16. The pump system of claim 14, further comprising:
   a pump segment comprising the tube, the pump segment configured for conveying the fluid based on compression of the pump segment generated by the pump;
   a pump segment frame comprising:
      a first end and a second end, wherein an inlet end of the pump segment is attached to the first end and an outlet end of the pump segment is attached to the second end, preventing said pump segment from stretching; and
      a visual placement indicator configured for facilitating proper placement of the pump segment frame in the pump housing.

17. The pump system of claim 14, wherein the non-pinching valve is configured to be actuated into an open position when the door of the pump is in a closed position.

* * * * *

UNITED STATES PATENT AND TRADEMARK OFFICE
CERTIFICATE OF CORRECTION

| | | |
|---|---|---|
| PATENT NO. | : 12,171,976 B2 | Page 1 of 1 |
| APPLICATION NO. | : 18/128639 | |
| DATED | : December 24, 2024 | |
| INVENTOR(S) | : George Mansour et al. | |

It is certified that error appears in the above-identified patent and that said Letters Patent is hereby corrected as shown below:

In the Claims

Claim 14, Column 10, Line 20, delete "fluid"

Signed and Sealed this
Eighth Day of April, 2025

Coke Morgan Stewart
*Acting Director of the United States Patent and Trademark Office*